US010080912B2

(12) United States Patent
Kwak et al.

(10) Patent No.: US 10,080,912 B2
(45) Date of Patent: Sep. 25, 2018

(54) MUCOSAL DOSE CONTROL RADIOTHERAPY APPARATUS USING MAGNETIC FIELDS

(71) Applicant: THE ASAN FOUNDATION, Seoul (KR)

(72) Inventors: Jung Won Kwak, Namyangju-si (KR); Nuri Hyun Jung, Daegu (KR); Kyoung Jun Yoon, Gimhae-si (KR); Byoung Chul Cho, Anyang-si (KR); Seung Do Ahn, Seoul (KR); Sang Wook Lee, Seoul (KR)

(73) Assignee: THE ASAN FOUNDATION, Seoul (KR)

( * ) Notice: Subject to any disclaimer, the term of this patent is extended or adjusted under 35 U.S.C. 154(b) by 189 days.

(21) Appl. No.: 14/976,945

(22) Filed: Dec. 21, 2015

(65) Prior Publication Data

US 2016/0175616 A1 Jun. 23, 2016

(30) Foreign Application Priority Data

Dec. 23, 2014 (KR) .................. 10-2014-0187083

(51) Int. Cl.
 *A61N 5/10* (2006.01)
 *A61B 90/00* (2016.01)

(52) U.S. Cl.
 CPC ......... *A61N 5/1065* (2013.01); *A61N 5/1043* (2013.01); *A61N 5/1048* (2013.01); *A61N 5/1067* (2013.01); *A61B 2090/363* (2016.02); *A61N 2005/1074* (2013.01); *A61N 2005/1087* (2013.01); *A61N 2005/1089* (2013.01)

(58) Field of Classification Search
 CPC ................... A61N 2005/1032–2005/1098
 See application file for complete search history.

(56) References Cited

U.S. PATENT DOCUMENTS

| | | | | |
|---|---|---|---|---|
| 2013/0188856 A1* | 7/2013 | Adler, Jr. | ................. | A61B 6/12 382/132 |
| 2013/0259198 A1* | 10/2013 | Alezra | ................. | A61N 5/1042 378/65 |
| 2014/0294154 A1* | 10/2014 | Slatkin | ................. | A61N 5/1042 378/65 |
| 2015/0297872 A1* | 10/2015 | Carpenter | ................. | A61N 5/10 600/1 |

FOREIGN PATENT DOCUMENTS

KR 101378447 B1 3/2014

OTHER PUBLICATIONS

Shani, "Radiation Dosimetry: Instrumentation and Methods," 2nd edition, CRC Press, 2001, p. 34-35.*

* cited by examiner

*Primary Examiner* — Thaddeus Cox
(74) *Attorney, Agent, or Firm* — Hauptman Ham, LLP

(57) ABSTRACT

A mucosal dose control radiotherapy apparatus using magnetic fields includes: a radiation generator irradiating radiation toward a tumor region of a patient; a magnetic field generator forming a magnetic field in a body of the patient; and a controller controlling a radiation dose transmitted from the radiation generator to the tumor region of the patient by adjusting a direction and a strength of the magnetic field of the magnetic field generator.

12 Claims, 5 Drawing Sheets

MUCOSAL DOSE CONTROL RADIOTHERAPY APPARATUS USING MAGNETIC FIELDS

CROSS-REFERENCE TO RELATED APPLICATION

This application claims priority from Korean Patent Application No. 10-2014-0187083, filed on Dec. 23, 2014 in the Korean Intellectual Property Office. The disclosure of the above patent is incorporated herein by reference in its entirety.

BACKGROUND

1. Field

Embodiments of the present invention relate to a mucosal dose control radiotherapy apparatus using magnetic fields, and more particularly, to a mucosal dose control radiotherapy apparatus using magnetic fields capable of treating a patient by optimizing a radiation dose distribution in a normal mucosa to thereby significantly reduce a side effect and transmitting a target radiation dose to a tumor region of a patient.

2. Description of the Related Art

A radiotherapy apparatus is a medical apparatus using radiation for treating diseases. Such a radiotherapy apparatus is widely used to delay or stop and further destroy a growth of a malignant tumor tissue such as cancer using charged radiation such as a photon, an electron, or a proton.

Meanwhile, in a case in which an overdose of radiation having high energy is transmitted to a non-tumor tissue of a body, that is, a normal body tissue, a deoxyribonucleic acid ("DNA") molecule is ionized to damage DNA, such that mutation of a gene or death of a cell is caused. Accordingly, the mutation resulting from the DNA damage may cause genetic defects or generate cancer.

In this regard, when a normal tissue and a tumor tissue are adjacent to one another, there may frequently occur a case in which a radiotherapy dose is not sufficiently irradiated due to a radiation side effect may frequently occur.

In particular, a body mucosa distributed in almost all regions of a body is one of the regions most sensitive to radiation. When a predetermined dose of radiation is transmitted to the mucosa, a side effect may occur in the mucosa, thereby posing a great limit to a radiotherapy.

Accordingly, at the time of radiotherapy, a radiation dose and a radiation dose distribution need to be accurately adjusted to allow a target tumor to receive a sufficient dose of radiation and to significantly reduce damage to a normal tissue.

In this regard, there is a need for a radiotherapy apparatus capable of treating a tumor by adjusting a radiation distribution in a mucosa region which is most sensitive to radiation using a regional magnetic field.

It is to be understood that this background of the technology section is intended to provide useful background for understanding the technology and as such disclosed herein, the technology background section may include ideas, concepts or recognitions that were not part of what was known or appreciated by those skilled in the pertinent art prior to a corresponding effective filing date of subject matter disclosed herein.

PRIOR ART DOCUMENT

Patent Document (Patent document 1) Korean Patent Application Registration No. 10-1378447 (Title of Invention: Magnetic Field Shielding Structure of MRI-based LINAC System, registration date: 2014 Mar. 20)

SUMMARY

Aspects of embodiments of the present invention are directed to a mucosal dose control radiotherapy apparatus using magnetic fields capable of treating a patient by optimizing a radiation dose distribution in a normal mucosa to thereby significantly reduce a side effect and transmitting a target radiation dose to a tumor region of a patient.

According to an exemplary embodiment of the present invention, a mucosal dose control radiotherapy apparatus using magnetic fields includes: a radiation generator irradiating radiation toward a tumor region of a patient; a magnetic field generator forming a magnetic field in a body of the patient; and a controller controlling a radiation dose transmitted from the radiation generator to the tumor region of the patient by adjusting a direction and a strength of the magnetic field of the magnetic field generator.

The magnetic field generator may form a uniform or non-uniform magnetic field area in all regions or a peripheral region of the body of the patient to which radiation is irradiated by the radiation generator.

The controller may further include a calculator calculating a radiation dose that is transmitted to the tumor region of the patient through the magnetic field.

The calculator may calculate the radiation dose that is transmitted to the tumor region of the patient based on the following Mathematical Equation 1:

$$D(x,y,z) = \iiint (TERMA(x',y',z') \times \text{Kernel}(x,x',y,y',z,z')) \, dx'dy'dz' \quad \text{[Mathematical Equation 1]}$$

wherein $D(x,y,z)$ denotes a radiation dose transmitted to the tumor region of the patient, $TERMA(x', y', z')$ denotes a total energy of an incident radiation beam that is reduced in a micro volume $dx'dy'dz'$, and $\text{Kernel}(x,x',y,y',z,z')$ denotes a dose ratio of a unit energy that is reduced in a micro volume $dx'dy'dz'$ being absorbed at a predetermined position $(x,y,z)$, and in this instance, Kernel in which the magnetic field formed by the magnetic field generator is evaluated is used.

The magnetic field generator may include one of an electromagnet, a permanent magnet, and a combination thereof.

The magnetic field generator may rotate around the patient or may be disposed in a fixed or movable manner around the patient.

The mucosal dose control radiotherapy apparatus may interwork with a positioning system using an image, and may be used in position correction of a patient and position correction of the magnetic field generator.

The mucosal dose control radiotherapy apparatus may have a degree of freedom that optimizes a dose by the magnetic field of the patient using a body-insertable prosthesis or a prosthesis material, wherein the prosthesis has a balloon shape including a prosthesis material therein or is a simple insertion type.

The prosthesis may be inserted along with adding a material favorable for imaging to verify and correct a state of the prosthesis using an image as well as for conversion of a shape of the mucosa or for conversion of a component for the optimization of a dose.

The foregoing is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The above and other features and aspects of the present disclosure of invention will be more clearly understood from the following detailed description taken in conjunction with the accompanying drawings, in which.

DETAILED DESCRIPTION

Hereinafter, exemplary embodiments with reference to a mucosal dose control radiotherapy apparatus using magnetic fields will be more clearly understood from the following description taken in conjunction with the accompanying drawings.

Figure 1:
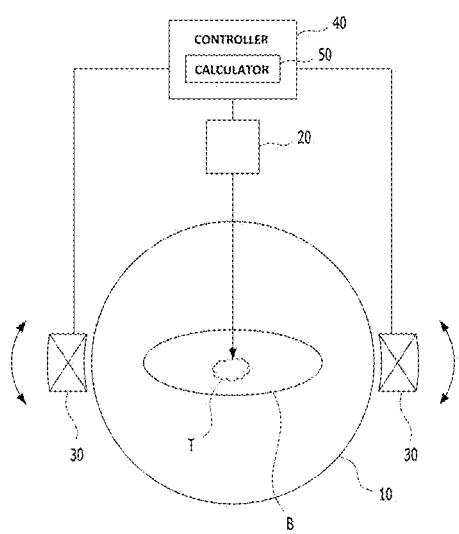
FIG. 1 is a schematic configuration view illustrating a mucosal dose control radiotherapy apparatus using magnetic fields according to an exemplary embodiment.

FIG. 1 is a schematic configuration view illustrating a mucosal dose control radiotherapy apparatus using magnetic fields according to an exemplary embodiment.

As illustrated in FIG. 1, the mucosal dose control radiotherapy apparatus using the magnetic fields according to an exemplary embodiment includes a radiation generator 20, a magnetic field generator 30, and a controller 40.

The radiation generator 20 is mounted in a shielding structure disposed outwardly of a bore 10 having a cavity therein, and irradiates radiation to a tumor region T of a patient B in the bore 10.

In such an embodiment, the radiation generator 20 may use a linear accelerator ("LINAC") which generates a megavoltage X-ray (MV X-ray). Based on a characteristic of an X-ray beam generated in an MV area, kinetic energy is transmitted to a secondary electron (hereinafter, referred to as "electron") and a radiation dose is transmitted to a body by the electron through a reaction occurring at a surface of a material subject to exposure due to a Compton effect.

The magnetic field generator 30 is mounted in another shielding structure disposed outwardly of the bore 10, and forms a magnetic field area in the patient B. The magnetic field generator 30 includes a pair of electromagnets or permanent magnets having different polarities and disposed to oppose one another while having the bore 10 therebetween.

In such an embodiment, the magnetic field generator 30 may form a magnetic field area in a region of the patient B between the radiation generator 20 and the tumor region T of the patient B, more particularly, a body cavity. In addition, the magnetic field generator 30 may include one of an electromagnet, a permanent magnet, and a combination thereof.

In the present exemplary embodiment, the magnetic field generator 30 including a pair of magnets are illustrated as rotating around an outer circumference of the bore 10, for example, around the patient B in the bore 10 to thereby increase a degree of freedom of a direction of the magnetic field. However, the magnetic field generator 30 is not limited thereto, and the magnetic field generator 30 including a plurality of magnets may be fixedly disposed around the patient B to thereby form a magnetic field area by one selected from the plurality of magnets through being controlled by the controller 40.

The controller 40 adjusts a direction and a strength of the magnetic field of the magnetic field generator 30, to thereby control a radiation dose transmitted from the radiation generator 20 to the tumor region T of the patient B. In other words, the controller 40 may adjust the direction of the magnetic field by allowing the magnetic field generator 30 to rotate around a circumference of the patient B in a desired manner.

In addition, the controller 40 controls an operation of the radiation generator 20.

Meanwhile, the controller 40 further includes a calculator 50 calculating the radiation dose that is transmitted to the tumor region T of the patient B through the magnetic field area.

The calculator 50 calculates the radiation dose that is transmitted to the tumor region T of the patient B based on Mathematical Equation 1.

$$D(x,y,z) = \iiint (TERMA(x',y',z') \times \text{Kernel}(x,x',y,y',z,z'))\, dx'dy'dz' \quad \text{[Mathematical Equation 1]}$$

In Mathematical Equation 1, D(x,y,z) denotes a radiation dose that is absorbed at a predetermined position (x,y,z), TERMA(x', y', z') denotes a total energy of an incident radiation beam that is reduced in a micro volume dx'dy'dz', and Kernel(x,x',y,y',z,z') denotes a dose ratio of a unit energy that is reduced in a micro volume dx'dy'dz' being absorbed at a predetermined position (x,y,z). In this instance, Kernel in which the magnetic field formed by the magnetic field generator 30 is evaluated is used.

Accordingly, by convoluting a TERMA value and a Kernel value with respect to a total volume of the radiation dose, the radiation dose that is absorbed at the predetermined position (x,y,z) may be calculated.

Meanwhile, since the TERMA value represents a total energy of an X-ray absent charge that is reduced, the TERMA value is not related to the magnetic field.

Further, since the Kernel value represents a spatial linear distribution by the electron generated in the reduction process, the Kernel value is absolutely affected by the magnetic field. In general, such a Kernel value is obtained by a computer simulation, and in particular, a spatially uniform magnetic field is generated by a computer simulation program to obtain a new Kernel value, and a Kernel deform map is obtained as in the following manner The Kernel deform map is represented by Mathematical Equation 2.

$$\text{Kernel}_{new}(B,x,x',y,y',z,z') = \text{Deform\_map}(\text{Kernel}(x,x',y,y',z,z'),B) \quad \text{[Mathematical Equation 2]}$$

Accordingly, the calculator 50 calculates a strength, a direction, and a magnitude of the magnetic field for optimizing a radiation dose distribution.

In an alternative exemplary embodiment, the calculator 50 may calculate based on a full Monte Carlo simulation method.

In other words, a toolkit capable of simulating a magnetic field is used, a history is constructed based on a probabilistic Monte Carlo method with respect to each particle, a spatial effect with respect to a dose of each of the histories is added up to calculate an overall dose distribution, and a radiation dose that is absorbed at a predetermined position may be calculated.

Based on such a configuration, a process of treating the tumor region T of the patient B using the mucosal dose control radiotherapy apparatus using the magnetic fields according to an exemplary embodiment will be described hereinbelow.

Figure 2:
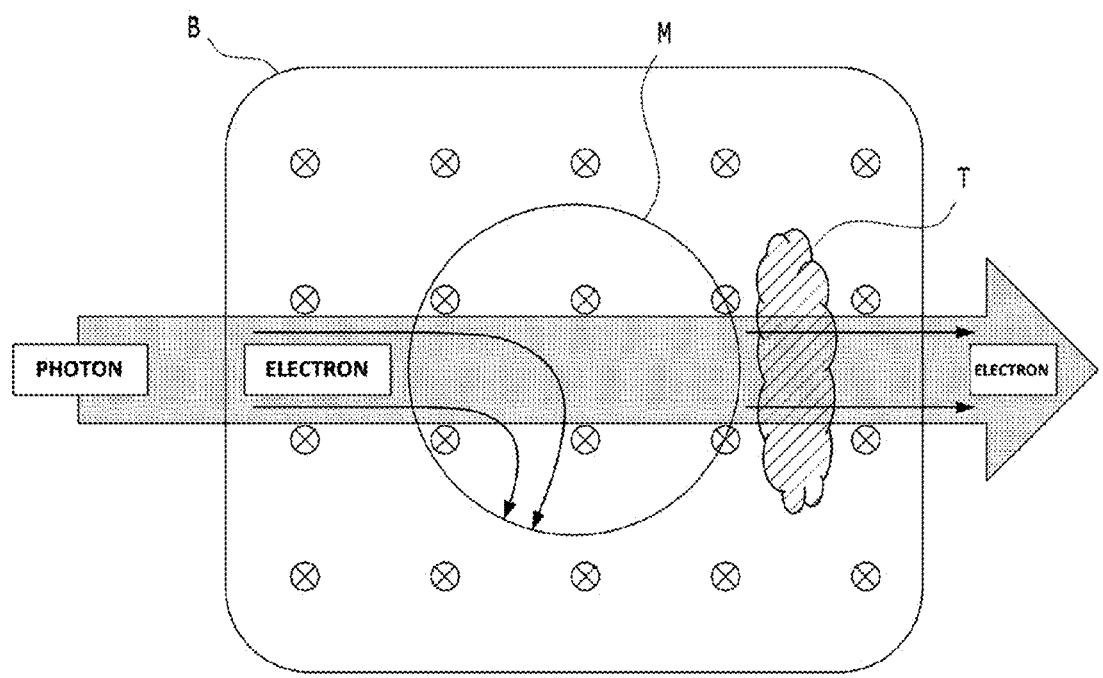
FIG. 2 is a schematic view illustrating an operation relationship between an electron and magnetic fields based on radiation in the mucosal dose control radiotherapy apparatus using the magnetic fields of FIG. 1.

In an exemplary embodiment, as illustrated in FIG. 2, treating the tumor region T in a case in which radiation is irradiated from the radiation generator 20 on a left side to the tumor region T on a right side, a magnetic field is operated in a direction of going into the ground, and an organ such as an empty digestive organ including a stomach, a small intestine, a large intestine, and the like, is disposed between the radiation generator 20 and the tumor region T will be described.

In a state in which the patient B having the tumor region T to be treated is lying down in the bore 10, the controller 40 controls the magnetic field generator 30 to operate such that the magnetic field generator 30 forms a magnetic field area in the body of the patient B.

The controller 40 controls the radiation generator 20 to operate such that the radiation generator 20 irradiates radiation to the tumor region T of the patient B.

In this instance, as the radiation generated from the radiation generator 20 passes through the body of the patient B, and charged particles, that is, electrons, are emitted. The emitted electrons serve to transmit high energy of radiation.

Meanwhile, the emitted electrons pass through the magnetic field area formed in the magnetic field generator 30, and in this instance, the emitted electrons receive a force by the magnetic field, for example, Lorentz's Force, so as to be polarized or dispersed in the magnetic field area.

In other words, as illustrated in FIG. 2, in the case that radiation is irradiated from the radiation generator 20 on the left side to the tumor region T on the right side, and the magnetic field is operated in the direction of going into the ground, a radiation photon generated from the radiation generator 20 on the left side passes through the body of the patient B to thereby emit electrons, and the emitted electrons, along with the photon, move to the tumor region T which is the target for the treatment through the magnetic field area in the direction in which radiation is irradiated.

In this case, while the emitted electrons pass through the magnetic field area, the controller 40 controls a direction and a strength of the magnetic field of the magnetic field generator 30 based on the calculation of the calculator 50, such that at least one of the electrons is polarized to one side due to Lorentz's Force, and an amount of the electrons corresponding to an appropriate radiation dose is transmitted to the target tumor region T through a mucosa M to thereby allow an appropriate dose of radiation to be irradiated to the tumor region T.

In other words, as the controller 40 controls the direction and the strength of the magnetic field of the magnetic field generator 30 subsequent to the calculation of the calculator 50, a portion of the emitted electrons is polarized or dispersed to an empty space within the organ, and the like, by radiation as illustrated in FIG. 2, a minimum amount of electrons is transmitted to a mucosa M of an organ at the front of the tumor region T.

Accordingly, a radiation dose transmitted to a normal tissue is significantly reduced, and an appropriate dose of radiation is transmitted to the tumor region T of the patient B, such that a side effect of radiation may be reduced, and a treatment effect may be enhanced.

Meanwhile, the electrons that have reached the target tumor region T through the magnetic field area and the mucosa M disturb tumor cells in the tumor region T, and the growth of the tumor cells is impeded or the necrosis of the tumor cells is caused, such that the tumor region T is treated.

Hereinafter, a test result of the mucosal dose control radiotherapy apparatus using the magnetic fields according to an exemplary embodiment will be described with reference to FIG. 3.

Figure 3:
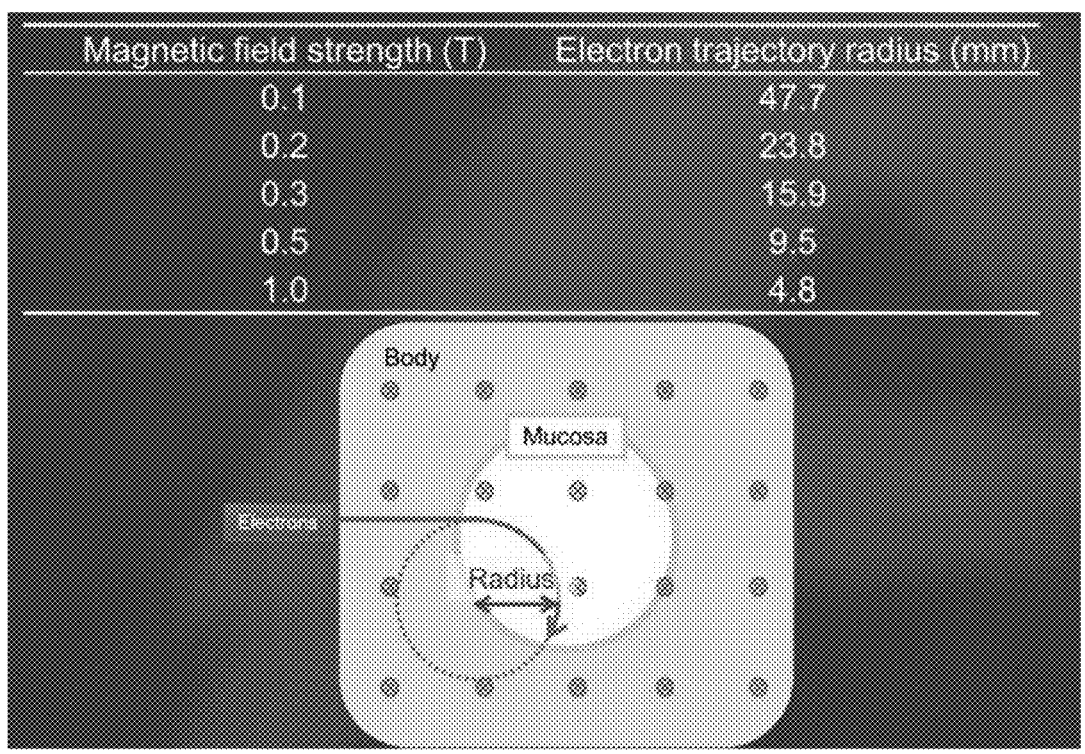
FIG. 3 is a graph illustrating test result data on a correlation between magnetic fields strength and an electron trajectory radius.

FIG. 3 is a graph illustrating electromigration in a magnetic field, e.g., test result data on a correlation between magnetic fields strength and an electron trajectory radius.

As illustrated in FIG. 3, when an electron moves from a left side to a right side, and a magnetic field is operated in a direction of going into the ground, an electron trajectory radius based on a magnetic field strength is measured in a state in which the electron is polarized in a counterclockwise direction with respect to the ground and a radiation strength is constant.

The test is conducted on the correlation between the magnetic field strength (unit: Tesla, T) and the electron trajectory radius (unit: millimeter, mm) at the time of radiation irradiation using a 6MV X-ray, and a result therefrom is represented in the Table in an upper portion of FIG. 3.

It may be verified from the Table in FIG. 3 that as the magnetic field strength increases, the electron trajectory radius decreases.

In other words, it may be verified from the Table in FIG. 3 that in a case of an organ having a relatively small diameter, as the magnetic field strength increases, the tumor region T may be treated without the mucosa M within the organ.

Meanwhile, there is a disadvantage of having to increase a size of a magnet in order to increase the magnetic field strength. Thus, the size of the magnet being manufactured needs to be limited based on the economic feasibility of a device.

Figure 4:
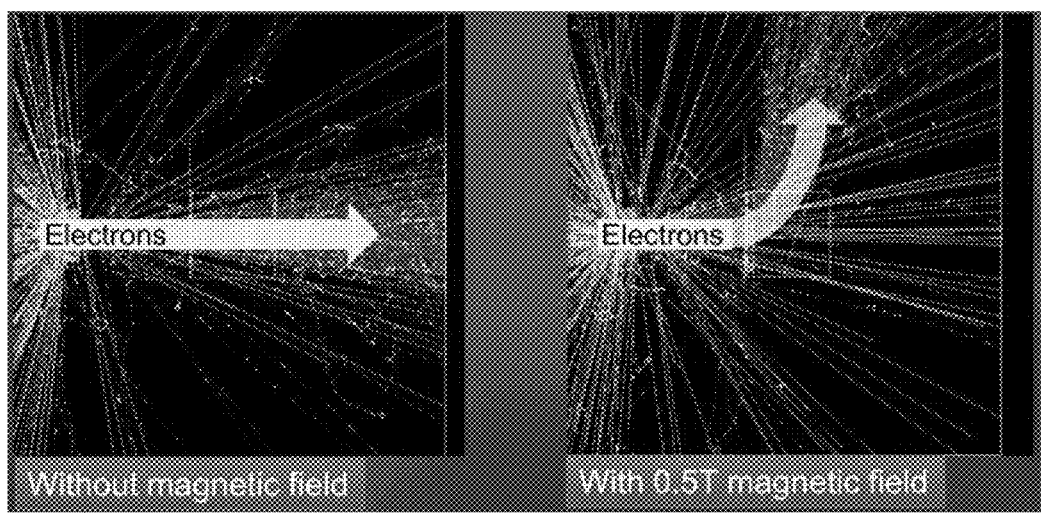
FIG. 4 is a view illustrating a simulation result of a flow of an electron generated during radiation based on a presence of a magnetic field area.

FIG. 4 is a view illustrating a simulation result of a flow of an electron generated during radiation based on a presence of a magnetic field area.

A left side of FIG. 4 illustrates a simulation performed on a flow of an electron when a 6MV X-ray is irradiated in an area absent a magnetic field whereas a right side of FIG. 4 illustrates a simulation performed on a flow of an electron when a 6MV X-ray is irradiated in a magnetic field area of 0.5 Telsa (T).

It may be verified from FIG. 4 that as the direction and the strength of the magnetic field of the magnetic field generator 30 are adjusted, at least one of the electrons emitted by radiation may be polarized or dispersed to an area.

Accordingly, in a case of an organ such as a digestive organ having a mucosa M therein, the direction and the strength of the magnetic field of the magnetic field generator 30 are adjusted so as to allow at least one of the electrons emitted by radiation to be polarized or dispersed to a hollow area in the organ at the time of radiation irradiation. Accordingly, a radiation dose transmitted to the target tumor region T may be maintained, and in addition thereto the damage to the mucosa M may be reduced.

Figure 5:
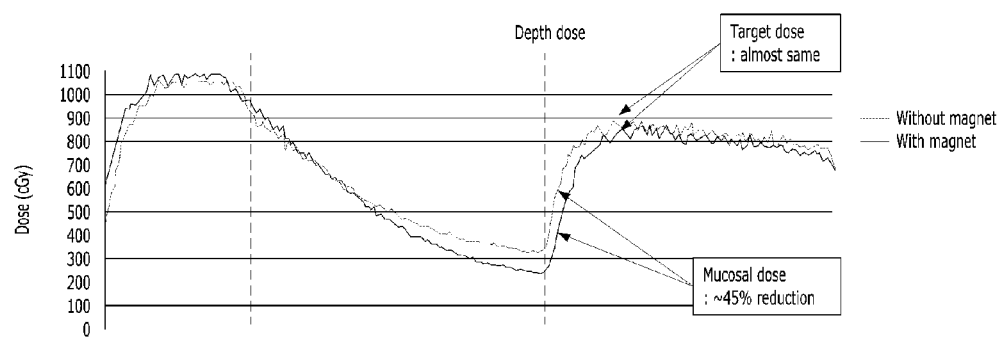
FIG. 5 is a graph illustrating a result of measuring a radiation dose in a tumor region using a mucosal dose control radiotherapy apparatus using magnetic fields according to an exemplary embodiment.

FIG. 5 is a graph illustrating a result of measuring a radiation dose in the tumor region T using the mucosal dose control radiotherapy apparatus using the magnetic fields according to an exemplary embodiment.

FIG. 5 illustrates a result of measuring a radiation dose based on a radiation irradiation depth in a case in which a 6MV X-ray is irradiated from the radiation generator 20 on the left side to the tumor region T on the right side through an organ having a diameter of 4 centimeters (cm) as illustrated in FIG. 2 and a magnetic field strength of 0.3 T is operated in a direction of going into the ground.

It may be verified from FIG. 5 that a radiation dose in the mucosa M of an organ at the front of the tumor region T is reduced by 45% as compared to a case in which a magnetic field area is not formed in a body.

In addition, it may be verified from FIG. 5 that the radiation dose in the target tumor portion T is similar in the case in which the magnetic field area is absent and in the case in which the magnetic field area is formed.

Accordingly, it may be verified from FIG. 5 that in a case in which the magnetic field area is formed in the body and radiation is irradiated thereto, the mucosal dose control apparatus using the magnetic fields according to an exemplary embodiment may reduce damage to the mucosa M because the radiation dose is significantly reduced in the mucosa M at the front of the tumor region T and a desired radiation dose is irradiated to the tumor region T so as to enhance a treatment effect.

As set forth above, according to one or more exemplary embodiments, radiation is irradiated to the tumor region of the patient simultaneously with the formation of the magnetic field area in the body of the patient, and the direction and the strength of the magnetic field in the magnetic field area are adjusted. Accordingly, an appropriate radiation dose is transmitted to the tumor region of the patient while a radiation dose transmitted to a normal tissue is significantly reduced, such that the side effect of radiation may be lessened and the treatment effect may be enhanced.

Meanwhile, the mucosal dose control apparatus using the magnetic fields according to an exemplary embodiment may interwork with a positioning system using an image, and may be used in position correction of the patient and position correction of the magnetic field generator.

In addition, the mucosal dose control apparatus using the magnetic fields according to an exemplary embodiment may have a degree of freedom that optimizes a dose by the magnetic field of the patient using a body-insertable prosthesis or a prosthesis material so as to adjust the position of the mucosa in the body of the patient. In this instance, the prosthesis may have a balloon shape including a prosthesis material therein or is a simple insertion type, corresponding to any tubular organ which allows insertion thereinto and other organs.

Meanwhile, the prosthesis may be inserted along with adding a material favorable for imaging to verify and correct a state of the prosthesis using an image as well as for conversion of a shape of the mucosa or for conversion of a component for the optimization of a dose.

From the foregoing, it will be appreciated that various embodiments in accordance with the present disclosure have been described herein for purposes of illustration, and that various modifications may be made without departing from the scope and spirit of the present teachings. Accordingly, the various embodiments disclosed herein are not intended to be limiting of the true scope and spirit of the present teachings. Various features of the above described and other embodiments can be mixed and matched in any manner, to produce further embodiments consistent with the invention.

What is claimed is:

1. A mucosal dose control radiotherapy apparatus using magnetic fields comprising:

a radiation generator configured to irradiate photon radiation, by passing through a body cavity of a patient and mucosa of the body cavity, toward a tumor region existing at a distance from under the mucosa of the body cavity of the patient;

a magnetic field generator configured to form a magnetic field in a body of the patient; and a controller configured to control a radiation dose transmitted from the radiation generator to the tumor region of the patient by adjusting a direction and strength of the magnetic field of the magnetic field generator, wherein the magnetic field generator is configured to form the magnetic field having a component perpendicular to a direction of the irradiated photon radiation, and wherein the controller is configured to control the magnetic field so that, at the body cavity, a secondary electron emitted from the irradiated photon radiation is dispersed into the body cavity by a Lorentz's force of the magnetic field, and at the tumor region, a secondary electron emitted from the irradiated photon radiation passed through the body cavity is provided to the tumor region.

2. The mucosal dose control radiotherapy apparatus of claim 1, wherein the magnetic field generator forms a uniform or non-uniform magnetic field area in all regions or a peripheral region of the body of the patient to which the photon radiation is irradiated by the radiation generator.

3. The mucosal dose control radiotherapy apparatus of claim 1, wherein the controller further comprises a calculator calculating a radiation dose that is transmitted to the tumor region of the patient through the magnetic field.

4. The mucosal dose control radiotherapy apparatus of claim 3, wherein the calculator is configured to calculate radiation dose absorbed at the predetermined position of the body based on a Full Monte Carlo Simulation Method having a toolkit capable of simulating a magnetic field.

5. The mucosal dose control radiotherapy apparatus of claim 1, wherein the magnetic field generator comprises one of an electromagnet, a permanent magnet, and a combination thereof.

6. The mucosal dose control radiotherapy apparatus of claim 1, wherein the magnetic field generator rotates around the patient or is disposed in a fixed or movable manner around the patient.

7. The mucosal dose control radiotherapy apparatus of claim 1, wherein the apparatus is configured to interwork with a positioning system using an image, and used in position correction of the patient and position correction of the magnetic field generator.

8. The mucosal dose control radiotherapy apparatus of claim 1, wherein the apparatus has a degree of freedom that optimizes a dose by the magnetic field of the patient using a body-insertable prosthesis or a prosthesis having a balloon shape including a prosthesis material therein.

9. The mucosal dose control radiotherapy apparatus of claim 8, wherein the prosthesis is inserted along with adding a material favorable for imaging to verify and correct a state of the prosthesis using an image as well as for conversion of a shape of the mucosa or for conversion of a component to optimize the dose.

10. The mucosal dose control radiotherapy apparatus of claim 1, wherein the controller is configured to control the magnetic field generator to deflect the secondary electron into the magnetic field in order to reduce a damage to a normal tissue in the body of the patient.

11. The mucosal dose control radiotherapy apparatus of claim 1, wherein the magnetic field is formed in an area between the radiation generator and the tumor region, the area including the body cavity.

12. A mucosal dose control radiotherapy apparatus using magnetic fields comprising:

a radiation generator configured to irradiate photon radiation toward a tumor region of a patient a magnetic field generator configured to form a magnetic field in a body of the patient a controller configured to control a radiation dose transmitted from the radiation generator to the tumor region of the patient by adjusting a direction and a strength of the magnetic field of the magnetic field generator; and a calculator calculating a radiation dose that is transmitted to the tumor region of the patient through the magnetic field wherein the controller is configured to control, by using the magnetic field, a secondary electron emitted from the irradiated photon radiation, in order to control the radiation dose, wherein the calculator calculates the radiation dose that is transmitted to the tumor region of the patient based on the following equation 1

$$D(x,y,z) = \iiint (TERMA(x',y',z') \times Kernel(x,x',y,y',z,z')\, dx'dy'dz'$$ [Equation 1]

where

D(x,y,z) denotes a radiation dose transmitted to the tumor region of the patient, TERMA(x', y', z') denotes a total energy of an incident radiation beam that is reduced in a micro volume dx'dy'dz', and Kernel(x,x',y,y',z,z') denotes a dose ratio of a unit energy that is reduced in a micro volume dx'dy'dz' being absorbed at a predetermined position (x,y,z), and wherein the Kernel(x,x',y,y',z,z') is obtained by using the magnetic field of the magnetic field generator.

* * * * *